US009676815B2

(12) United States Patent
Lenna et al.

(10) Patent No.: US 9,676,815 B2
(45) Date of Patent: *Jun. 13, 2017

(54) PROCESS FOR THE PREPARATION OF ABIRATERONE OR ABIRATERONE ACETATE (71) Applicant: INDUSTRIALE CHIMICA S.R.L., Milan (IT)

(72) Inventors: Roberto Lenna, San Giorgio su Legnano (IT); Riccardo Di Brisco, Trecate (IT)

(73) Assignee: INDUSTRIALE CHIMICA S.R.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/908,721

(22) PCT Filed: Jul. 23, 2014

(86) PCT No.: PCT/EP2014/065813
§ 371 (c)(1),
(2) Date: Jan. 29, 2016

(87) PCT Pub. No.: WO2015/014686
PCT Pub. Date: Feb. 5, 2015

(65) Prior Publication Data
US 2016/0168191 A1    Jun. 16, 2016

(30) Foreign Application Priority Data

Jul. 29, 2013  (WO) .................. PCT/IB2013/056206
Nov. 8, 2013   (IT) .............................. MI2013A1861

(51) Int. Cl.
C07J 1/00    (2006.01)
C07J 43/00   (2006.01)
C07J 31/00   (2006.01)
(52) U.S. Cl.
CPC ........... *C07J 43/003* (2013.01); *C07J 31/006* (2013.01)
(58) Field of Classification Search
CPC ............................... C07J 1/0011; C07J 43/003
USPC ........................................................ 540/95
See application file for complete search history.

(56) References Cited

FOREIGN PATENT DOCUMENTS

WO        93/20097 A1    10/1993
WO      2006/021777 A1    3/2006

OTHER PUBLICATIONS

International Search Report for PCT/Ep2014/055813 dated Nov. 6. 2014 (3 pages).
Sun, Q., et al., "Pd(PPh3)4/AgOAc-catalyzed coupling of 17-steroidal triflates and alkynes: Highly efficient synthesis of D-Ring unsaturated 17-alkynylsteroids," Steroids, Elsevier Science Publishers, New York, NY, US, vol. 75, No. 12, pp. 936-943 (Dec. 1, 2010).
Navendu, Jana, et al., "Development of a Suzuki Cross-Coupling Reaction between 2-Azidoarylboronic Pinacolate Esters and Vinyl Triflates to Enable the Synthesis of [2,3]-Fused Indole Heterocycles," The Journal O Forganic Chemistry, vol. 79, No. 6, pp. 2781-2791 (Mar. 21, 2014).
Gerard A. Potter, et al., "A Convenient, Large-Scale Synthesis of Abiraterone Acetate [3B-Acetoxy-17-(3-Pyridyl)Androsta-5, 16-Diene], A Potential New Drug for the Treatment of Prostate Cancer,"Organic Preparations and Procedures Int., 29(1):123-134 (1997).

*Primary Examiner* — Brenda Coleman
(74) *Attorney, Agent, or Firm* — Abelmam, Frayne & Schwab (57) ABSTRACT

The present invention relates to a novel process for the synthesis of abiraterone and in particular abiraterone acetate, a compound of formula (I) reported below: having pharmacological activity suitable for slowing down the progression of advanced stage prostate cancer. The process is characterized by the fact that the intermediate triflation step is carried out on prasterone (DHEA) or its 3-acetate using Ar—N(OTf)$_2$ as the triflation reagent, but where Ar is not phenyl, and by the fact that the base used in this step is an alkali metal alcoholate.

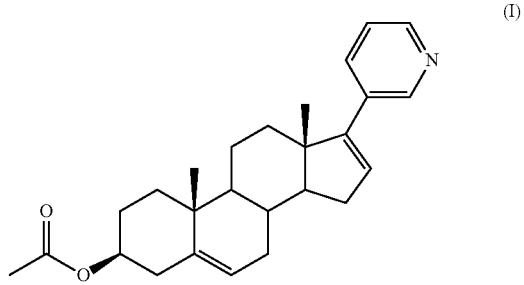

(I)

7 Claims, 4 Drawing Sheets

PROCESS FOR THE PREPARATION OF ABIRATERONE OR ABIRATERONE ACETATE

RELATED APPLICATIONS

This application is a national phase of Application No. PCT/EP2014/065813 filed Jul. 23, 2014, and claims priority from PCT/IB2013/056206 filed Jul. 29, 2013 and Italian Patent Application No, MI2013A001861 filed Nov. 8, 2013, all incorporated by reference in theft entirety.

FIELD OF THE INVENTION

The present invention relates to the field of processes for the synthesis of active ingredients for pharmaceutical use, and in particular to a process for the preparation on an industrial scale of abiraterone or abiraterone acetate.

PRIOR ART

The compound of formula (I) reported below, the chemical name of which is (β)-17-(pyridin-3-yl)androsta-5,16-dien-3-ol acetate, is commonly designated by the name of abiraterone acetate:

(I)

Abiraterone acetate is a steroid having pharmacological activity suitable for slowing down the progression of advanced stage prostate cancer.

Prostate carcinoma is the main tumour in the male population of Western countries, where it is also the second cause of death by cancer. The cells of advanced stage prostate cancer are capable of autonomously synthesising testosterone starting from cholesterol, providing by themselves for their own growth and development thanks to enzyme CYP17, a key member in the synthesis of androgens and, in particular, testosterone.

Abiraterone acetate is an efficient inhibitor of enzyme CYP17 and thus a drug capable of strongly inhibiting the production of testosterone and other androgen hormones acting at the level of adrenal glands, testis and most especially the tumour microenvironment.

This compound has shown to be capable of extending the life of patients suffering from prostate cancer, as well as of improving their quality of life, and is the progenitor of a new class of non-chemotherapeutic drugs having a targeted action, capable of directly acting against the self-sustaining process of the tumour.

Abiraterone acetate has been described for the first time in the international patent application WO 93/20097 A1. Example 1 of this application describes the preparation of abiraterone acetate (I) from prasterone acetate (III) according to the following scheme:

Prasterone acetate
(III)

(II)

Abiraterone acetate
(I)

wherein the intermediate (II), 3β-acetoxyandrosta-5,16-dien-17-yl-trifluoromethanesulphonate, is obtained by the reaction of prasterone acetate (III) with trifluoromethanesulfonic anhydride in methylene chloride in the presence of 2,6-di-t-butyl-4-methylpyridine as a base; in formula (II) reported above, the abbreviation "Tf" indicates the radical —$SO_2CF_3$; the abbreviation shall also be used with the same meaning in the remainder of the description.

The intermediate (II) recovered by silica gel flash chromatography is reacted with diethyl-(3-pyridyl)borane in the presence of a palladium (II) catalyst to yield abiraterone acetate. The recovery of the product takes place by silica gel flash chromatography as well.

An alternative synthesis is described in the article "A convenient, large-scale synthesis of abiraterone acetate [3β-acetoxy-17-(3-pyridyl)androsta-5,16-diene], a potential new drug for the treatment of prostate cancer", G. A. Potter et al., *Organic Preparations and Procedures Int.,* 29(1), 123-134 (1997). According to the authors this novel preparation would overcome the problem, unsolved by the previously described syntheses, of a large scale production of abiraterone. The synthetic scheme (reported below) actually seems to have little industrial applicability, not so much for the fact that the reactions involved are four with respect to the two reactions of the synthesis of WO 93/20097 A1, but rather because the reactant needed to obtain the intermediate "hydrazone" is hydrazine, a known carcinogenic product.

prasterone · hydrazone · iodine · abiraterone abiraterone acetate

In the international patent application WO 2006/021777 A1 there is described and claimed an optimisation to the process of WO 93/20097 A1, based on the study of the reaction conditions. According to the inventors (WO 2006/021777 A1, page 3) the process described keeps within levels defined as acceptable, the formation of the impurity of formula:

eliminating the need for chromatographic purifications. The formation of the impurity in any case is not completely avoided and there remains a need for purifications at the end of the process to eliminate it.

A key item of this new process is the selection of the base to use in the reaction from prasterone acetate (III) to intermediate (II), which is selected among the tertiary or heterocyclic amines pyridine, 2,6-lutidine, N-methylmorpholine, trimethylamine, triethylamine, 1,4-diazabicyclo[2.2.2]octane (DABCO), N,N-diisopropylethylamine (DIPEA), 1,8-diazabicycloundec-7-ene (DBU) and 1-azabicyclo[2.2.2]octane (commonly referred to as quinuclidine). The formation of the intermediate (II) is obtained in this process with a yield of 60% (Example "Triflate formation 3", page 14 of WO 2006/021777 A1); the reported yield is in fact 80% of a 3:1 mixture of intermediate (II) and starting prasterone acetate. The Example "Salt formation" on page 15 describes the formation of the methanesulphonate of abiraterone as a purification method of the latter from the unreacted portion of prasterone. Also in this case the proposed synthesis route does not appear to have actual industrial applicability: as one can read in the Example, the obtained salt is crystallized from isopropanol, but in these conditions an ester of methanesulfonic acid is formed, and it is known that these esters are genotoxic and must therefore be eliminated from the final product.

The article "Pd(PPh$_3$)$_4$/AgOAc-catalyzed coupling of 17-steroidal triflates and alkynes: Highly efficient synthesis of D-ring unsaturated 17-alkynylsteroids", Q. Sun et al., Steroids, 75 (2010) 936-943, by describing the coupling reaction between 17-steroidal triflates and alkynes reports that the triflation reaction conducted in tetrahydrofuran (THF) at −78° C. in the presence of PhN(Tf)$_2$ and potassium hexamethyldisilazane (known with the abbreviation KHMDS) provides better results with respect to the use of triflic anhydride Tf$_2$O in methylene chloride with NaH or pyridine. In view of these results, the chemist could have therefore considered the modification of the known abiraterone (or abiraterone acetate) production processes, adopting the conditions of the article of *Steroids* in the triflation reaction; the experimental tests described in the following part of the article, however, show that in these conditions an improvement of the triflation reaction is obtained indeed, but the resulting abiraterone acetate contains the impurity, the formula of which is shown below, which cannot be eliminated:

The problem of purity of the abiraterone acetate obtainable according to the teachings of the cited article of *Steroids* remains also if, using potassium hexamethyldisilazane as a base, the triflating agent is changed.

Accordingly, since the ultimate goal of the process is not the improvement of an intermediate step thereof, but the synthesis of abiraterone or abiraterone acetate of a pharmaceutical quality, the process conditions described in this article turn out in fact unsuitable for the goal.

Therefore, there is still in the art a need of arranging a process for synthesizing abiraterone or abiraterone acetate of actual applicability on an industrial scale.

SUMMARY OF THE INVENTION

The present invention relates to a novel process for the production of abiraterone or abiraterone acetate according to the scheme:

said process comprising:
  a first step consisting in the reaction of prasterone or prasterone acetate (III) with an aromatic bis(trifluoromethanesulfonimide) of general formula Ar—N(Tf)$_2$, wherein Ar indicates an aromatic radical other than phenyl and the group N(Tf)$_2$ is the radical:

in the presence of a base selected from the alcoholates of alkali metals; and
  a second step consisting in the reaction of the mixture resulting from said first step with diethylpyridylborane in the presence of a palladium (II) catalyst.

In the reaction scheme reported hereinabove, compound (III) is prasterone when X is hydrogen, and is prasterone acetate when X is the acetyl radical, CH$_3$—C(O)—; similarly, compound (I) is abiraterone when X=H, and is abiraterone acetate when X=CH$_3$—C(O)—.

The synthesis process of the present invention avoids the formation of the impurity of which, by the process of WO 2006/021777 A1, it is only possible to limit the amount.

DETAILED DESCRIPTION OF THE INVENTION

The present invention relates to a novel process for the production of abiraterone or abiraterone acetate wherein is fundamental the reaction of the first step, the reaction of prasterone or prasterone acetate (III) with an aromatic bis(trifluoromethanesulfonimide) of general formula Ar—N(Tf)$_2$ in the presence of a base selected from alkali alcoholates to obtain the intermediate of formula (II); the bis (trifluoromethanesulfonimides) are commonly known in the art with the abbreviation triflimides. The thus obtained intermediate (II) is then further reacted in the second step of the process into the desired product.

The aromatic radical of triflimide Ar—N(Tf)$_2$ used in the first step may be of any type, excluding the unsubstituted benzene ring; for example, it may be a mono- or polycyclic aromatic radical, of the hydrocarbon, heterocyclic or mixed type, made from a heterocyclic ring fused to a hydrocarbon ring, which in this latter case may also be saturated; the Ar radical may also be substituted. The preferred triflimides for the purposes of the invention are those corresponding to the general formulas (IV) or (V) reported below (IV)

(V)

wherein:
R1, R2, R3, R4 and R5, independently, may be hydrogen, halo, —NO$_2$, a linear or branched alkyl radical, an amide radical RC(O)NH— or an alkoxy radical RO—, wherein R is a linear or branched alkyl group, provided that R1, R2, R3, R4 and R5 cannot be all hydrogen atoms at the same time;
and
one of R6, R7, R8, R9 and R10 is the radical —N(Tf)$_2$, while the remaining radicals among R6 and R10, independently, have the same meanings reported hereinabove for radicals R1-R5.

Preferably Ar—N(Tf)$_2$ is N-(2-pyridyl)-bis(trifluoromethanesulfonimide).

The amount of triflimide is between 0.8 and 2 times the weight of the starting prasterone acetate.

The reaction solvent is selected from toluene, xylene, diethyl ether, methyl tertbutyl ether, tetrahydrofuran (THF), methyl tetrahydrofuran, chloroform, dichloromethane and 1,2-dichloroethane. Preferred solvents are ethers, for example tetrahydrofuran.

The base that may be used is an alcoholate of an alkali metal, preferably sodium tert-butylate or potassium tert-butylate.

The reaction temperature is between −80° C. and 30° C., while the reaction time is between 2 and 24 hours.

Once the intermediate of formula (II) is obtained, this may be transformed into abiraterone or abiraterone acetate (I) in the second step of the process, reacting the mixture resulting from the first step described hereinabove with diethylpyridylborane in the presence of a palladium (II) catalyst such as, for example, bis(triphenylphosphine)palladium(II) dichloride, Pd(PPh$_3$)$_2$Cl$_2$.

The formed abiraterone acetate is separated from the reaction mixture by means of salification with an acid; then, the abiraterone acetate is recovered by treatment with an aqueous base, and the product obtained is purified by known methods, such as solvent-based crystallisation or silica gel chromatography.

The invention is further illustrated by the following examples, reported as illustrating and non-limiting examples of the present invention.

The reactants used in the examples are of common commercial availability and are employed without the need of further purifications.

For the analytic controls by means of thin-layer chromatography (TLC) are used silica gel TLC plates 60 F$_{254}$ on aluminium sheet or silica gel HPTLC 60 F$_{254}$ with a concentration zone, from Merck.

The HPLC chromatograms are recorded with an Agilent 1200 model chromatograph by elution with a gradient of methanol/water from 85/15 to 100/0 on C18 analytical column; 150 mm×4.6 mm; 2.7 µm. The detector is UV (λ=220 nm). The RRT values reported in the examples for some impurities indicate the relative retention times and represent the retention time of the peak corresponding to the specific impurity divided by the retention time of the peak corresponding to the desired product.

The HPLC-MS chromatograms are recorded with an Agilent 1100 model chromatograph coupled to an API 2000 model mass spectrometer from Applied Biosystem. The ionisation of the sample is obtained by acidification of the mobile phase with formic acid (chemical ionisation).

All the concentrations of solutions indicated with a percentage value shall be considered as weight values, unless otherwise stated.

EXAMPLE 1

This example illustrates a preparation of abiraterone acetate (I) starting from prasterone acetate (III) according to the invention.

A solution of 25.3 g of potassium tert-butylate and THF (1 l) is stirred for 30 minutes keeping the temperature at below −70° C. Under stirring prasterone acetate (50 g) is added. Then, N-(2-pyridyl)-bis(trifluoromethanesulfonimide) (65 g) is added portion-wise and is kept under stirring at a temperature between −70 and −80° C. for 2 hours. The cold solution is poured onto a biphasic solution consisting of isopropyl acetate (1 l) and a 25% ammonium chloride aqueous solution (800 ml).

The phases are separated and the organic phase is washed with 800 ml of 25% sodium acetate aqueous solution and then with an aqueous solution of sodium chloride (800 ml). A part of the solvent is distilled off at reduced pressure obtaining the precipitation of a white solid which is eliminated by filtration. The residual solution is concentrated to oil still at reduced pressure. The oil thus obtained is crystallized from the mixture methanol/triethylamine. The obtained sample (49 g) verified in HPLC (λ=220 nm) against authentic sample is intermediate (II) with 98.7% purity.

48 g of intermediate (II) is dissolved in THF (980 ml), then bis(triphenylphosphinepalladium(II)dichloride Pd(PPh$_3$)$_2$Cl$_2$ (1.46 g), diethyl(pyridyl)borane (23 g) and an aqueous solution of sodium carbonate (240 ml, 43.5 g sodium carbonate) are added under stirring at 20-25° C. Reflux is kept for 2 hours, further 370 mg of bis(triphenylphosphinepalladium(II)dichloride Pd(PPh$_3$)$_2$Cl$_2$ is added and the reflux is continued for further 45 minutes. Transformation is complete (TLC check).

Cooling down to 20-25° C. is performed and isopropyl acetate (1 l) and water (850 ml) are added.

The phases are separated, the organic phase is concentrated at reduced P after filtration and washing with water. A dark oil (62.4 g) is obtained which is then dissolved in methanol (180 ml). The solid obtained is filtered which turns out to be unreacted diethyl(pyridyl)borane.

The methanolic solution is concentrated at reduced P and the residue re-dissolved in isopropyl acetate (315 ml). The solution, pre-cooled down at a temperature between 0 and 5° C., is then treated with oxalic acid dihydrate (26 g). Stirring is performed at a temperature between 0 and 5° C. for 1 hour then the solid is filtered and washed with isopropyl acetate.

The abiraterone acetate oxalate thus obtained is stirred at a temperature between 0 and 5° C. with methylene chloride (300 ml) and an aqueous solution of sodium bicarbonate (500 ml, 40 g) obtaining a complete solution.

The phases are separated and the organic phase is concentrated to dry product at reduced P.

The solid obtained is crystallized from methanol obtaining, after drying, 20.5 g of abiraterone acetate (RT=7.021, 99.85% HPLC purity, λ=220 nm).

Figure 1:
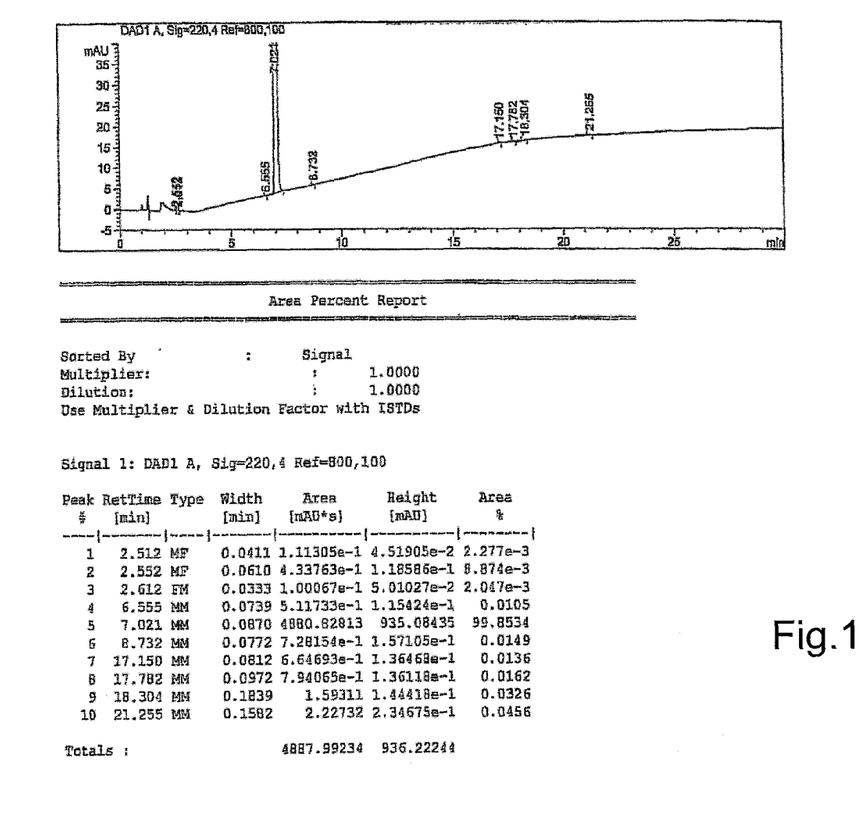
FIG. 1 shows a chromatogram, along with the peak listing thereof, of the product obtained according to the process of the invention.

All the impurities detectable by the HPLC chromatogram reported in FIG. 1 have a % area lower than 0.05. The presence of abiraterone, which is considered an impurity of abiraterone acetate by the European Pharmacopoeia, is not detectable.

EXAMPLE 2

This example illustrates a preparation of abiraterone acetate (I) on an industrial scale starting from prasterone acetate (III) according to the invention.

51 kg of potassium tert-butylate in THF (760 kg) and prasterone acetate (100 kg) are stirred at a temperature below −70° C. Then N-(2-pyridyl)-bis(trifluoromethanesulfonimide) (133 kg) is added maintaining the stirring for 2 hours at a temperature between −70 and −80° C.

The cold solution is poured onto a biphasic solution consisting of isopropyl acetate (360 kg) and a 10% ammonium chloride aqueous solution.

The phases are separated and the organic phase is first washed with an aqueous solution of ammonium chloride, then with 450 kg 10% sodium acetate aqueous solution, and eventually with an aqueous solution of sodium chloride.

A part of the solvent is distilled off at reduced pressure obtaining the precipitation of a solid which is eliminated by filtration. The residual solution is then distilled until obtaining an oil which is crystallized from the mixture methanol/triethylamine.

The sample obtained after drying (112 kg) verified in HPLC (λ=220 nm) against an authentic sample is intermediate (II) with 98.14% titer.

112 kg of intermediate (II) is dissolved in THF (1079 kg), then bis(triphenylphosphinepalladium(II)dichloride Pd(PPh$_3$)$_2$Cl$_2$ (3.2 kg), diethyl(pyridyl)borane (129.3 kg) and an aqueous solution of sodium carbonate are added under stirring at 20-25° C.

Reflux is kept for 1 hour (TLC check), further 400 g of bis(triphenylphosphinepalladium(II)dichloride Pd(PPh$_3$)$_2$Cl$_2$ is added, obtaining complete transformation (TLC check) after further 30 minutes of reaction.

Cooling down to 20-25° C. is performed, the phases are separated by washing the organic phase with an aqueous solution of sodium chloride.

The organic phase is then distilled until obtaining a dark oil which is then solubilized with methanol, recovering by fractional crystallization the excess diethyl(pyridyl)borane.

Methanol is eliminated by distillation, the residue is dissolved in isopropyl acetate, then the solution is filtered after treatment with decolorising carbon and silica gel.

The solution, adjusted at T=20±5° C., is then treated with oxalic acid dihydrate (60 kg).

Stirring is performed at T=20±5° C. for 8 hours and then the solid is filtered and washed with isopropyl acetate.

The abiraterone acetate oxalate obtained is stirred at a temperature between 0 and 5° C. with methylene chloride (880 kg) and an aqueous solution of sodium bicarbonate.

The phases are separated and the organic phase is distilled.

The solid obtained is dissolved in isopropyl acetate, then treated with Quadrasil® (registered trademark of Johnson Matthey Finland Oy) for 6 hours, for the removal of the catalyst; the Quadrasil® scavengers, sold by Sigma-Aldrich, consist of porous silica beads having defined pore size, wherein the silica surface is functionalised with metal binders, and allow a quick and effective removal of traces of metals from aqueous or organic solutions.

After filtration, a part of the solvent is distilled off, cooling down to 0±5° C. is performed obtaining the crystallisation of the product.

The abiraterone acetate obtained after drying (65 kg) meets the specifications reported in the corresponding chapter of the European Pharmacopoeia.

EXAMPLE 3 (Comparative)

This example illustrates the preparation of abiraterone acetate from prasterone acetate, wherein the triflation reaction is carried out according to procedures derived from the article *Steroids*, 75 (2010) 936-943.

A solution obtained dissolving 50 g of prasterone acetate and 64.9 g of N-phenyl-bis(trifluoromethanesulfonimide) (Ph-N(Tf)$_2$) in 750 ml tetrahydrofuran is cooled down to −78° C. under stirring. 303 ml of a 0.5 M solution of potassium hexamethyldisilazane in toluene are slowly added and maintained under stirring for 2 hours at a temperature between −80 and −70° C. The reaction mixture is then brought to a temperature between 0 and 5° C. and maintained as such for additional 30 minutes.

750 ml isopropyl acetate and 1152 ml aqueous solution saturated with ammonium chloride are added. The phases are separated and the organic phase is washed with 1600 ml 1M HCl aqueous solution and with 1600 ml aqueous solution saturated with NaCl.

The solvent is eliminated at reduced pressure obtaining a dark oil (132.7 g).

The raw oil obtained is then crystallized from ethanol (312 ml) obtaining, after drying, 64.8 g of solid product.

60 g of such product, dissolved in 650 ml tetrahydrofuran, are added, under stirring and at a temperature between 20 and 25° C., with bis(triphenylphosphine)palladium(II)dichloride (Pd(PPh$_3$)$_2$Cl$_2$, 637 mg), diethyl(pyridyl)borane (20 g) and 179 ml 2 M aqueous solution of sodium carbonate. Reflux is kept at about 70° C. for 2 hours. Cooling is performed down to a temperature between 20 and 25° C. and isopropyl acetate (660 ml) and water (660 ml) are added.

The phases are separated, the organic phase is washed with 20% NaCl aqueous solution, filtered with decolorising carbon and concentrated at reduced pressure.

The product obtained is then dissolved in methanol at 45° C. (200 ml) eliminating by filtration the reprecipitated solid which turns out to be unreacted diethyl(pyridyl)borane; at a HPLC control, the product shows a purity of 99.1% (chromatogram recorded at 220 nm). The methanolic solution is concentrated at reduced pressure.

The residue, controlled by HPLC, shows, inter alia, the presence of an impurity with RRT=1.257; this residue is solubilized again in isopropyl acetate at 45° C. (164 ml) eliminating by filtration the undissolved part.

The solution is concentrated at a final volume of 120 ml, and is cooled down to 0<T<5° C. 12.6 g of phosphoric acid is added by cold stirring for 3 hours. The solid thus formed is filtered and solubilized with 350 ml of basic aqueous solution (5% NaHCO₃) and 400 ml of methylene chloride (DCM). Stirring at a temperature between 0 and 5° C. is performed for 2 hours, then it is checked that the pH of the aqueous phase is basic (pH of about 8). The phases are separated and the organic phase, after washing with water, is anhydrified and concentrated to dry product at reduced pressure.

The obtained solid (26.4 g) is repeatedly crystallized from methyl isobutyl ketone obtaining, after drying, 9 g of abiraterone acetate.

Figure 2:
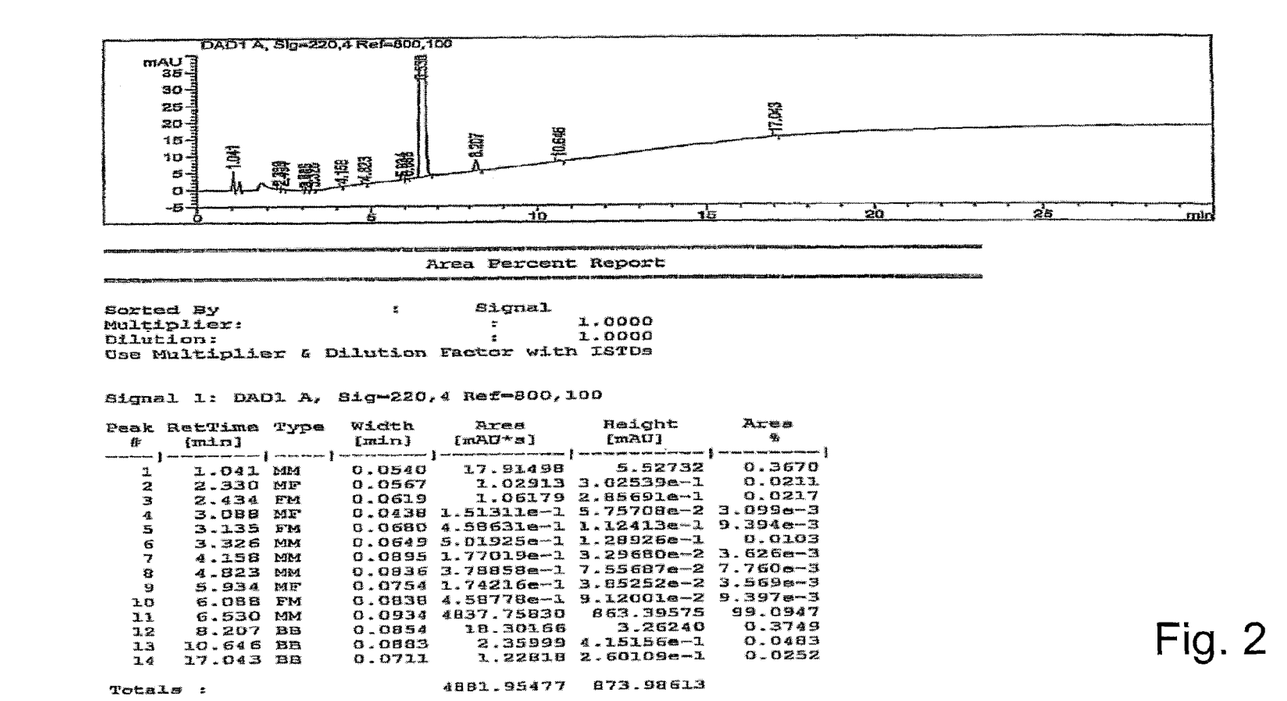
FIGS. 2, 3 and 4 show chromatograms, along with the peak listings thereof, of products obtained according to processes of the prior art.

The product controlled by means of HPLC shows a purity of 99.1% (chromatogram shown in FIG. 2, recorded at 220 nm), and as the main impurity a peak at RRT=1.257 having area 0.375%.

Figure 3:
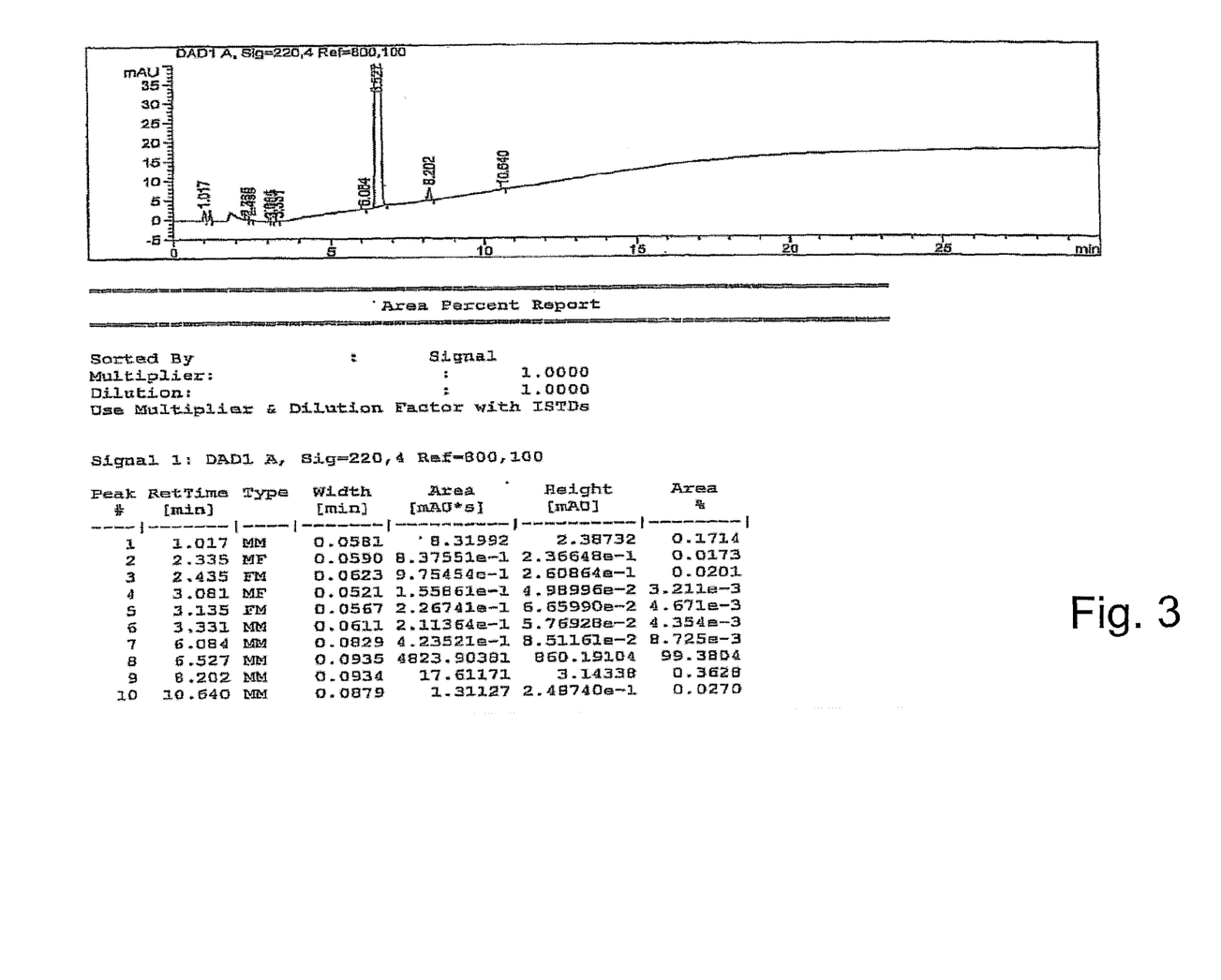

The HPLC-Mass analysis indicates that such impurity has a molecular weight of 405 amu, in accordance with the following structure:

In order to try and eliminate the impurity shown hereinabove, the sample of abiraterone acetate is further crystallized from methanol. The product obtained, controlled by means of HPLC, shows a purity of 99.4% (chromatogram shown in FIG. 3, recorded at 220 nm).

The impurity with RRT=1.257 retains a % area of 0.363, almost unchanged with respect to the value before purification.

EXAMPLE 4 (Comparative)

This example illustrates a complete preparation of abiraterone acetate starting from prasterone acetate using as a base potassium hexamethyldisilazane according to the description of *Steroids,* 75 (2010) 936-943.

A solution of 18.11 g potassium hexamethyldisilazane and THF (400 ml) is stirred for 30 minutes keeping the temperature at below −70° C. Under stirring prasterone acetate (20 g) is added. Then, N-(2-pyridyl)-bis(trifluoromethanesulfonimide) (23.85 g) is added portion-wise and is kept under stirring at a temperature between −70 and −80° C. for about 2 hours. The cold solution is poured onto a biphasic solution consisting of isopropyl acetate (800 ml) and a 25% ammonium chloride aqueous solution (800 ml).

The phases are separated and the organic phase is washed with 800 ml of 25% sodium acetate aqueous solution and then with an aqueous solution of sodium chloride (800 ml).

The organic solution is concentrated to oil still at reduced pressure. The oil thus obtained is treated with 84 ml heptane obtaining the precipitation of a solid which is eliminated by filtration. The organic part is then concentrated at reduced pressure and the residue is crystallized from the mixture ethanol/triethylamine.

The sample obtained (21 g) verified by HPLC (λ=220 nm) against authentic sample is intermediate (II).

20.7 g of such intermediate (II) are dissolved in THF (230 ml), then bis(triphenylphosphinepalladium(II)dichloride (Pd (PPh₃)₂Cl₂, 283 mg), diethyl(pyridyl)borane (8.9 g) and an aqueous solution of sodium carbonate (80 ml, 16.8 g of sodium carbonate) are added under stirring at 20-25° C. After 2 hours, further 35 mg of Pd(PPh₃)₂Cl₂ are added.

Reflux is kept until complete transformation (TLC check). Cooling down to 20-25° C. is performed and isopropyl acetate (500 ml) and water (250 ml) are added.

The phases are separated, the organic phase is concentrated at reduced P after filtration and washing with water. A dark oil (20.5 g) is obtained which is then dissolved in methanol. The solid obtained is filtered which turns out to be unreacted diethyl(pyridyl)borane.

The methanolic solution is concentrated at reduced P and the residue re-dissolved in methyl isobutyl ketone (80 ml). The solution, pre-cooled down at a temperature between 0 and 5° C., is then treated with oxalic acid dihydrate (7 g).

Stirring is performed at a temperature between 0 and 5° C. for 1 hour and then the solid is filtered and washed with methyl isobutyl ketone.

The obtained abiraterone acetate oxalate is stirred at a temperature between 0 and 5° C. with methylene chloride (150 ml) and an aqueous solution of sodium bicarbonate (150 ml, 20 g) obtaining a complete solution. The phases are separated and the organic phase is concentrated to dry product at reduced P. The solid obtained is crystallized several times from methyl isobutyl ketone obtaining, after drying, 7.5 g abiraterone acetate (98.6% HPLC purity recorded at λ=220 nm).

Figure 4:
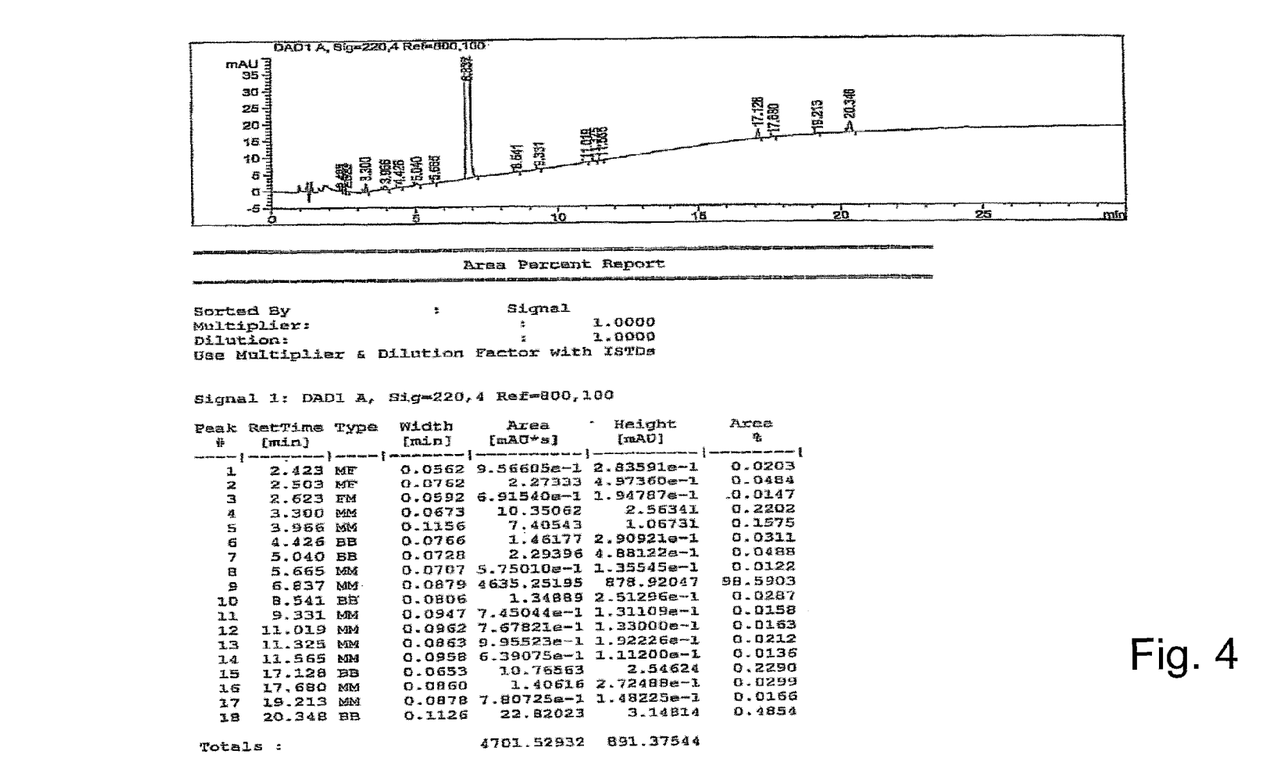

The HPLC chromatographic profile (chromatogram shown in FIG. 4) shows a number of impurities with % area greater than 0.10, among which the highest (RRT=2.98) having % area of 0.48.

Comment on Results

As shown by the test results, operating according to the method of the invention, abiraterone acetate having high purity is obtained which is suitable for the envisaged pharmaceutical usage. Vice versa, operating according to the procedures which may be derived from the cited article, *Steroids,* 75 (2010) 936-943, such result is not achieved.

The invention claimed is:

1. A process for preparing abiraterone or abiraterone acetate of formula I:

(I)

wherein X is H or CH$_3$—C(O)—, comprising:
(i) reacting prasterone or prasterone acetate of formula III:

(III)

wherein X is as above, with an aromatic bis (trifluoromethane sulphonamide) of formula Ar—N(Tf)$_2$, wherein Ar is an aromatic radical other than phenyl, and N(Tf)$_2$ is:

in the presence of an alcoholate of an alkali metal, to form:

wherein X is as above, and
(ii) reacting the compound of formula II with diethylpyridylborane in the presence of a palladium(II) catalyst, to form abiraterone or abiraterone acetate.

2. The process of claim 1, wherein said aromatic bis (trifluoromethanesulfonimide) has formula (IV) or (V):

(IV)

(V)

wherein:
R1, R2, R3, R4 and R5, independently, may be hydrogen, halo, —NO$_2$, a linear or branched alkyl radical, an amide radical RC(O)NH— or an alkoxy radical RO—, wherein R is a linear or branched alkyl group with the proviso that that R1, R2, R3, R4 and R5 cannot be all hydrogen atoms at the same time;
and
one of R6, R7, R8, R9 and R10 in formula (V) is -(Tf)$_2$, wherein the remaining radicals R6, R7, R8, R9, and R10, independently, have the same meanings as do R1, R2, R3, R4, and R5.

3. The process according to claim 2, wherein said bis (trifluoromethanesulfonimide) is N-(2-pyridyl)-bis(trifluoromethanesulfonimide).

4. The process according to claim 1, wherein said bis (trifluoromethanesulfonimide) is used in an amount ranging from 0.8 to 2 times the weight of prasterone or prasterone acetate.

5. The process according to claim 1, wherein said base is selected from the group consisting of sodium tert-butylate and potassium ten-butylate.

6. The process according to claim 1, wherein (i) is carried out at a reaction temperature between −80° C. and 30° C. for a reaction time of from 2 to 24 hours.

7. The process according to claim 1, wherein the palladium (II) catalyst is bis(triphenylphosphine)palladium(II) dichloride, Pd(PPh$_3$)$_2$Cl$_2$.

* * * * *